(12) United States Patent
Michalek et al.

(10) Patent No.: US 9,125,962 B2
(45) Date of Patent: Sep. 8, 2015

(54) WASTE PROCESSING APPARATUS AND METHOD FEATURING WATER REMOVAL

(75) Inventors: Jan Michalek, Pataskala, OH (US); Theodore Thomas, Columbus, OH (US)

(73) Assignee: ESTECH USA, LLC, Canal Winchester, OH (US)

( * ) Notice: Subject to any disclaimer, the term of this patent is extended or adjusted under 35 U.S.C. 154(b) by 369 days.

(21) Appl. No.: 11/716,101

(22) Filed: Mar. 9, 2007

(65) Prior Publication Data

US 2008/0217444 A1    Sep. 11, 2008

(51) Int. Cl.
*B02C 19/00* (2006.01)
*A61L 11/00* (2006.01)

(52) U.S. Cl.
CPC ....................................... *A61L 11/00* (2013.01)

(58) Field of Classification Search
USPC ........................... 241/23, 65, 299, 284, 18, 21
See application file for complete search history.

(56) References Cited

U.S. PATENT DOCUMENTS

| | | | |
|---|---|---|---|
| 228,542 A | 6/1880 | Lister | |
| 986,180 A | 3/1911 | Koenig | |
| 1,381,802 A | 6/1921 | Copelin | |
| 1,536,894 A | 5/1925 | Lillie | |
| 3,477,581 A * | 11/1969 | Stearns | ...................... 210/195.3 |
| 4,342,830 A | 8/1982 | Holloway | |
| 4,540,495 A | 9/1985 | Holloway | |
| 4,844,351 A | 7/1989 | Holloway | |
| 4,974,781 A | 12/1990 | Placzek | |
| 5,116,363 A | 5/1992 | Romweber et al. | |
| 5,119,994 A | 6/1992 | Placzek | |
| 5,190,226 A | 3/1993 | Holloway | |
| 5,253,764 A | 10/1993 | Gement | |
| 5,300,438 A | 4/1994 | Augspurger et al. | |
| 5,361,994 A | 11/1994 | Holloway | |
| 5,407,809 A | 4/1995 | Finn | |
| 5,427,650 A | 6/1995 | Holloway | |
| 5,540,391 A | 7/1996 | Anderson | |
| 5,556,445 A | 9/1996 | Quinn et al. | |
| 6,328,234 B1 * | 12/2001 | Saucier et al. | ..................... 241/1 |
| 6,397,492 B1 | 6/2002 | Malley | |
| 6,752,956 B1 * | 6/2004 | Vanderwal | ........................ 422/3 |
| 7,347,391 B2 * | 3/2008 | Michalek et al. | ............... 241/23 |
| 2004/0250700 A1 | 12/2004 | Renaud | |
| 2005/0035032 A1 | 2/2005 | McGee | |
| 2005/0059849 A1 | 3/2005 | Liu | |

FOREIGN PATENT DOCUMENTS

WO    WO 03/025101    3/2003

* cited by examiner

*Primary Examiner* — Mark Rosenbaum
(74) *Attorney, Agent, or Firm* — Standley Law Group LLP

(57) ABSTRACT

The present invention includes an apparatus and method for processing solid waste products. The invention features periodic removal of water preferably while the contents are under pressure. The apparatus comprises a rotatably mounted cylindrical vessel having a first end, a second end and an interior surface, at least one end terminating in a hatch that may be opened to allow access to the interior of the vessel and sealably closed to allow pressurization of the vessel; a steam inlet for injecting stem disposed at one or both ends; and one or more valves for exhausting water periodically as the waste mass is being processed.

12 Claims, 10 Drawing Sheets

WASTE PROCESSING APPARATUS AND METHOD FEATURING WATER REMOVAL

TECHNICAL FIELD

The present invention relates to the treatment of municipal solid waste and the like.

BACKGROUND OF THE INVENTION

The present invention relates to systems and methods for treating process material and, more particularly, to systems and methods for treating municipal solid waste material, medical waste material, reclaimed paper and the like.

As a result of increasing scarcity of landfills and more stringent environmental regulations, efforts have been made to reduce the volume of process material, such as municipal solid waste ("MSW") and paper material, such as newsprint and other reclaimed and recycled paper products as a step in the process of disposing of the material, either by depositing it in landfills, incinerating it or recycling it.

Systems and methods have been developed to break down such material for disposal, or in the case of paper products, use as insulation.

An example of such a process and device is U.S. Pat. No. 5,190,226, which discloses an apparatus and method for separation, recovery and recycling of MSW. The apparatus includes a rotating drum which is fed at an upstream end by a reciprocating ram, a steam source which is connected to introduce high temperature steam into the drum, and a spiral rib or flight mounted within the drum to transport material deposited in an upstream end of the drum along the length of the drum.

Another example is described in U.S. Pat. No. 5,119,994 that describes a steam treatment vessel held stationary, preferably at an angle to the horizontal.

One of the disadvantages of the arrangements of the prior art is that portions of the waste product charge in the vessel become compacted, either passively by maintaining the vessel at a fixed position with respect to the horizontal, or actively through the use of spiral or helical rib arrangements that urge portions of the charge against active surfaces in a horizontal direction (or a direction parallel to the longitudinal axis of the vessel) as the vessel is rotated. In some instances, the compacted portions of the waste product charge cause portions of the waste product charge to be sequestered from the steam treatment environment.

Another disadvantage of the prior art is that prior systems and methods do not allow for the most advantageous control and distribution of energy placed into the vessel, and its efficient transfer to the waste charge mass. In addition, each charge of waste products will vary in its constituents, and thereby in its heat capacity and in its energy requirements for effective treatment. In methods of the prior art, either the process parameters (temperature, pressure, or time) had to be varied with each charge of waste, or the consistency of the processed product (i.e., particle size, moisture content, degree of break down and processing generally) varied with batch to batch. This made an economically and technically viable industrial process for the treatment of waste less than efficient.

Accordingly, it is also advantageous to be able to determine the heat capacity of a given charge of waste products thereby to determine the energy requirements for effective treatment of that charge, in order treatment can be carried out with higher efficiency.

One method of attempting to reach achieve more efficient treatment is described in U.S. Pat. No. 6,397,492 and involves the continual supply of steam during loading, while simultaneously rotating the vessel, so as to break down the waste during loading to a material of roughly uniform density, so that the same mass of waste is processed in each batch. However, this process requires a separate steam treatment during loading which results in greater overall time requirements for each waste batch.

Accordingly, there remains a need for methods that allow for greater time and energy efficiency while allowing the process of waste in charges that vary in weight and constituents.

In addition, it is also desirable to be able to reduce the amount of water in the processed waste mass to make it amenable for further processing into fuel pellets. As excess water typically must be removed by active drying, this requires additional time and energy investment. Accordingly, another aspect of the present invention addresses the need to efficiently remove excess water, especially that in the interstitial spaces of the waste material mass.

The present invention accordingly represents an improvement over prior art apparatus and methods, such as those described in U.S. Pat. Nos. 5,540,391; 5,116,363; 5,253,764; 5,190,226; 5,361,994; 5,427,650; 5,407,809; and 6,397,492, and in published European Patent Application No. 02758620.5; all of which are incorporated herein by reference. The present invention also represents an improvement over co-pending application Ser. No. 11/122,341, which is hereby incorporated by reference.

SUMMARY OF THE INVENTION

The present invention includes an apparatus for processing solid waste products, the apparatus comprising a rotatably mounted cylindrical vessel having a first end, a second end and an interior surface, at least one end terminating in a hatch that may be opened to allow access to the interior of the vessel and sealably closed to allow pressurization of the vessel; a steam inlet for injecting stem disposed at one or both ends; a plurality of substantially straight blades protruding from the interior surface of the vessel, and each the blade extending substantially the entire length of the vessel, so as to be capable of transporting waste material from the bottom of the vessel toward the top of the vessel while rotating, and releasing the waste material to fall to the bottom of the vessel; and at least one actuator for moving the vessel between a position wherein the first end is higher than the second end and a position wherein the second end is higher than the first end (that is, such that the vessel is moved between a position wherein the first end is directed upward from the horizontal, and a position wherein the second end is directed upward from the horizontal).

The vessel may be supported in any fashion that allows this movement. It is preferred that the vessel be supported by a hinged fulcrum point about which it may be moved.

The vessel further includes at least one door or hatch, or similar means to access the interior of the vessel for loading and unloading the waste charge, which may be transported to the vessel by a conveyor or other traditional means.

The apparatus includes a means for rotating the vessel, such as those known and used in the art, such as trunnion rings and rollers, or chain-driven gear and sprocket systems or a "spud" ring. Any stable method of rotating the vessel at a controlled speed would be suitable. The rotation of the vessel however must also be able to accommodate its movement by the actuator(s) as described herein.

The arrangement of the blades and the interior of the vessel preferably are such that there are essentially no surfaces against which the charge of waste products may become compressed laterally during rotation of the vessel; i.e., in a direction parallel to the longitudinal axis of the vessel; and that an open central region is provided through substantially the entire length of the vessel (i.e., the treatment space of the vessel). Such an arrangement permits portions of the charge of waste products to be transported from the bottom of the vessel toward the top of the vessel during rotation, and released to fall to the bottom of the vessel through the pressurized steam environment as discreet relatively low density portions to increase the surface area of that portion with respect to the steam environment of the vessel.

In an alternative embodiment, the blades may be arranged such that adjacent pairs of blades converge toward opposite ends of the vessel. In this variation, it is preferred that each blade be provided with a slight twist along its length such that it provides a slight time between the fall of the portion of the mass on the upper end of the blade as it rises toward the top of the vessel upon rotation, with respect to the portion of the mass on the relatively lower end of the blade. In this regard, the blades are slightly twisted such that ends of adjacent blades that converge are twisted away from one another while ends of adjacent blades that diverge are twisted toward one another.

The vessel will have many of the same characteristics of those known and used in the art, in terms of being designed to contain large quantities of matter (i.e., several tons) and to hold those contents under pressure.

The steam inlet(s) is/are provided with steam by steam conduits that are adapted to accommodate movement and rotation of the vessel. The steam conduits may be any conduit material appropriate for the transmission of high pressure steam. The conduits are flexible or otherwise provided with sufficiently flexible or articulated joints to accommodate the movement and rotation of the vessel, and are typically controlled by one or more valves for selectively introducing steam into and out of the vessel during the processing of the waste. The steam may be provided at any location along the length of the vessel, and several arrangements are known for providing a number of steam inlets along the length of such a vessel. However, the simplest arrangement is to provide steam inlets at one or both ends of the vessel. The steam provided to the vessel may be saturated steam or super-heated steam, and may be provided statically or as a stream through the vessel, or even if the form of discreet steam pulses into the vessel, such as pulses of super-heated steam.

The actuators may be any apparatus capable of moving the vessel between a position wherein the first end is higher than the second end and a position wherein the second end is higher than the first end. The actuator typically is adapted to move the vessel between a position wherein the first end is higher than the second end and a position wherein the second end is higher than the first end at such a rate so as to be capable of leveling a charge of solid waste products disposed therein. Examples may include hydraulic actuators and mechanical screw actuators, which may be provided in pairs disposed respectively on either side of the gravitational center of the vessel. The actuators may be for instance, linear mechanical screw actuators, such as those commercially available under the name Joyce ComDrive from Joyce of Dayton, Ohio, and those commercially available from Duff-Norton of Charlotte, N.C.

The apparatus may also include load sensors independent of or associated with the actuator(s). The load sensors may be of any type capable of sensing and recording loads of the magnitude typically associated with waste treatment vessels of the type of the present invention.

The apparatus optionally includes a microprocessor or PLC controller associated with the load sensors, the microprocessor or PLC controller having programming instructions so as to determine the load distributed within the vessel, such as at the position of each of the actuators. The microprocessor or PLC controller further may be adapted to signal the actuators in response to changes in the distribution of a charge of waste products contained in the vessel.

The apparatus may also include a plurality of thermocouples or thermometers disposed along the length of the vessel. These may have a microprocessor or PLC controller associated with them, the microprocessor or PLC controller having programming instructions adapted to calculate the amount of energy absorbed by a charge of waste products contained in the vessel over time.

The apparatus may also include a control system to operate the vessel system and may comprise a computer program code product that controls a computer comprising one or more central processor units (CPUs) interconnected to a memory system with peripheral control components, such as for example, a Pentium® microprocessor, commercially available from Intel Corporation, Santa Clara, Calif.

Most preferably the apparatus has load sensors associated with or independent of the actuator(s), the load sensors adapted to determine the mass of a charge of waste products contained in the vessel, and a microprocessor or PLC controller having programming instructions so as to determine the energy absorption per mass of a charge of waste products contained in the vessel.

The apparatus also includes at least one motor or other means for rotating the vessel. The motor(s) may be connected to the vessel through appropriate drive/transmission means. For instance, the motors may be connected to drive sleeves that surround the vessel, as shown in the figures. Typically, the motor and drive means will be mounted in such an arrangement so as to move along with the movement of the vessel itself, such as by being mounted on a moveable frame supporting the vessel.

Apparatus with Tip-Leveling Actuator Only

Still another variation of the present invention is an apparatus for processing solid waste products, comprising: a rotatably mounted cylindrical vessel having a first end, a second end and an interior surface, at least one end terminating in a hatch that may be opened to allow access to the interior of the vessel and sealably closed to allow pressurization of the vessel; a steam inlet for injecting stem disposed at least one of the ends; a plurality of substantially straight blades protruding from the interior surface of the vessel, and each blade extending substantially the entire length of the vessel (i.e., the contained volume that provides steam treatment and movement of the waste charge), so as to be capable of transporting waste material from the bottom of the vessel toward the top of the vessel, and releasing the waste material to fall to the bottom of the vessel; and at least one actuator for moving the vessel between a position wherein the first end is higher than the second end and a position wherein the second end is higher than the first end.

Apparatus with Agitating Leveling Means Only

Yet another variation of the present invention is an apparatus for processing solid waste products, the apparatus comprising: a rotatably mounted cylindrical vessel having a first end, a second end and an interior surface, at least one end terminating in a hatch that may be opened to allow access to the interior of the vessel and sealably closed to allow pressurization of the vessel; a steam inlet for injecting stem disposed at least one of the ends; and at least one actuator for agitating the vessel so as to be capable of leveling a charge of solid waste products disposed therein.

The apparatus of the present invention may also include one or more valves to remove water from the vessel during processing. The water may be evacuated to atmospheric pressure, or may even be evacuated under the influence of vacuum.

Method of Treating Waste Involving Free Fall Through Low Density Zone

The present invention also includes a method of processing solid waste products in a vessel having a central longitudinal axis, comprising: loading the vessel with a charge of solid waste products along the bottom of the vessel, the vessel having a plurality of substantially straight blades extending from the interior surface of the vessel and each blade extending substantially the entire length of the vessel; sealing the vessel; introducing steam into the vessel; rotating the vessel so as to cause the charge of solid waste products to be moved from the bottom of the vessel to toward the top of the vessel and allowed to fall through the vessel so as to maintain a low density region of waste substantially along the length of the vessel; and thereafter depressurizing the vessel and unloading the processed waste therefrom.

Typically, the solid waste products are moved from the bottom of the vessel to toward the top of the vessel and allowed to fall in a series of discreet portions through a relatively low density region of the interior of the vessel.

It is preferred that the vessel is rotated without substantial compression of the charge of solid waste products along a direction parallel to the central longitudinal axis.

Another preferred aspect of the present method is that the solid waste products are transported back and forth along a direction parallel to the central longitudinal axis while the vessel is being rotated. This results in both longitudinal agitation and active leveling of the charge. This may be accomplished by tilting the vessel using the actuators, and/or by action of the plurality of blades when the configuration is used wherein the blade pairs converge toward opposite ends.

It is most preferred that the blades be provided in pairs that converge in alternating fashion toward opposite ends of the vessel to provide an additional side-to side movement of the waste charge mass. Further, the blades may be provided with a twist about their longitudinal axis such that a time delay is provided between the descent of the portions of the waste charge mass that are raised by the relatively higher portion of each angled blade, and the portions of the waste charge mass that are raised by the relatively lower portion of each angled blade, as the vessel rotates.

It is most preferred that the steam is introduced from both ends of the vessel, and most preferred that the steam is superheated steam introduced in pulses into the vessel using appropriate valve and pressure release systems.

In another preferred variation of the method of the invention, the mass distribution of the charge of solid waste products is measured while the vessel is rotating, and, optionally the energy absorbed by the charge of solid waste products is measured while the vessel is rotating.

The method of the present invention may also feature measuring the mass distribution of the charge of solid waste products and measuring the energy absorbed by the charge of solid waste products while the vessel is rotating, and determining the time required to treat the charge of solid waste products from the amount of energy absorbed by the charge of solid waste products over time. This determination in turn allows the operator to conclude the treatment of the charge of solid waste products based on time at temperature, rather than on a fixed schedule, providing a higher quality result. This may be done by the operator or automatically through feedback control from the microprocessors or PLC controllers.

The apparatus and method of the present invention offers advantages over prior systems that featured helical or augur arrangements designed to move the charge of solid waste products from one end of the vessel to the other, or other interior arrangements that feature surfaces disposed perpendicular to the longitudinal axis of the vessel. These arrangements often result in compression of portions of the waste product charge, preventing the efficient and complete treatment of those portions.

The apparatus and method of the present invention in contrast permits the formation of a zone that extends the length of the vessel by leveling the load prior to treatment initiation or shortly after the start of treatment. The blades of the apparatus of the present invention take portions of the waste product charge and successively raise them and allow them to fall through this low density zone, without substantial compression of any portion of the waste product charge, such as is brought about by transportation of the charge along the longitudinal axis of the vessel, or by maintaining the vessel in a titled position with respect to the horizontal.

In addition, the apparatus and method of the present invention allows both the load and temperature of zones within the vessel to be monitored.

Water Removal Method

The present invention also includes a method of control of the amount of water present throughout the cycle of processing solid waste products in a vessel, comprising: (1) loading the vessel with a charge of solid waste products along the bottom of the vessel; (2) sealing the vessel; (3) introducing steam into the vessel so as to pressurize the vessel; (4) rotating the vessel so as to cause the charge of solid waste products to be moved from the bottom of the vessel to toward the top of the vessel, whereby liquid water typically collects at the bottom of the vessel; (5) periodically removing aliquots of liquid water (as water or steam) from the vessel, preferably while the vessel remains pressurized; and (6) thereafter depressurizing the vessel and unloading the processed solid waste therefrom.

Under normal operating conditions, the water in the vessel normally will be in a superheated condition such that upon being exhausted it will become steam. The water typically will be removed from a point at or near the bottom of the vessel, or at least from a point below the upper boundary of the waste mass, as can be seen in FIG. 8.

There are a range of materials collectively known as lignin. Generally accepted ranges for the glass transition temperature of lignin focus on 240-295° F. as the beginning range for wood softening. Most thermochemical pulping is carried out in the range of 212-338° F. (lower temperatures make longer fibers: higher temperatures remove more lignin). The use of a high temperature, such as in our range, has the dual advantage of producing short fibers (for easy separations) and low lignin fibers (again, making post treatment separations easier while providing a higher quality fiber product for post-processing uses).

In the method of the present invention, it is preferred to maintain a temperature below 356° F. to retain the valuable hemicellulose in the fibers, and below about 338° F. to prevent plastics decomposition, but as high as possible for rapid and complete removal of the various lignin components.

In accordance with the present invention, steam is injected into the vessel to raise its temperature by the transfer of latent and sensible heat from the steam to the vessel contents and walls, to reach effective levels of heat and pressure for waste processing. The vessel contents, when comprising waste stream material, are typically about 28% moisture, and warm up as steam condenses. As the steam is continuously added, eventually (in accordance with prior methods), the temperature and pressure rise to a saturated condition, typically more than 50 psia and above about 302° F. In accordance with prior methods, after the time at temperature is realized, the pressure in the boiler is released, and the vessel and its contents equilibrate to a temperature at water boiling point by flashing off (evaporating) some of the water in the vessel. Prior art processes have resulted in a cooked product with higher water content than was found in the original MSW. More recently, systems have been developed that feature a vessel wherein the steam heat is added via a closed jacket, preventing contact with the steam. This offers some advantages for water management, but at a major complication in the expense of the equipment and in the time necessary to raise the temperature.

The present invention preferably uses higher temperatures (typically 300 to 335° F.) and pressures (typically 70-110 psia) for the autoclaving process. A substantially dryer final product can be created as a consequence of operating the vessel at a higher design temperature and pressure, combined with the drainage of free water during the vessel operations. A relatively higher-temperature operation results in more water evaporation during the end-of-cycle steam flash, such that the extra evaporation offsets the extra water added (as steam) to reach a higher final temperature. As a consequence, to achieve a dryer product one would be encouraged to operate the vessel at a temperature as high as otherwise allowed (110 psia gauge/335° F.).

Additional dryness derives from the in-process water drain that is another aspect of the present invention. One might conclude that the sensible heat used to raise vessel water to temperatures in excess of boiling is recovered at the end of the cycle when the excess sensible heat is converted latent heat by boiling off some of the water. While that is conceptually correct, thermodynamic models show that a higher state of product dryness occurs as a result of draining free water at the end of the cycle, prior to depressurization. Such draining reduces the mass of water available for evaporation during depressurization: modeling of a typical system under ideal circumstances shows that the vessel water concentration can be lowered, for instance, from its original 27% to a final 21% (even less if water in the MSW is freed during the process).

It is estimated that the water concentration in the residual fiber should be 11-12% if condensate is first drained off.

The present invention includes the removal of water prior to steam flashing, energy savings derive from removing free water at lower temperatures, whether continuously during the cycle or at stages within the cycle. In this regard, the vessel may be provided with a vacuum pump (or similar system) to be activated after the steam flash, such that even further percentage water may be removed. The vacuum pump may also be applied to remove some free water during the initial pump down.

The method of the present invention may be carried out using an apparatus of the present invention. The vessel of the present invention may be provided with at least one valve along one side of the vessel. In the case of the vessel of the present invention, is preferred that the valve is on one or both ends such that the vessel may be titled from the horizontal to move the liquid water toward one end of the vessel for most efficient exhaustion, and from the bottom of the vessel or at least from a point below the upper boundary of the waste mass. It is also preferred that the water may be exhausted under vacuum using airtight fittings placed on the valve(s), and drawing upon the valve(s) using vacuum pumps (or similar systems).

The water concentration in the residual fiber should be about 50% following the high temperature steam removal: lower temperature operations would increase that to 55% or more. Typically, the water concentration in the residual fiber should be 11-12% if condensate is first drained off.

With one exception, prior disclosed art uniformly teaches the removal of pressure and steam from a rotating autoclave vessel through the coaxial drain(s) on the vessel centerline. This process provides the opportunity to remove pressurized steam and any free water present above the location of the valve, and such steam that may be generated as the consequence of the release of pressure.

The sole exception in prior art is thermomechanical pulping system. In TMP, a surfeit of water is used to wash the pulp fibers, and in one patent, an underdrain is provided to for the sole purpose of removing excess free water prior to removal of the wet pulp.

Experience shows that the vessel contents after cooking MSW consist of metal products, broken glass, "dirt", coalesced plastic products, degraded cellulose fibers, and water (containing water contaminants). When there is a screened drain at the bottom of the vessel, the dirt, metal products, and degraded cellulose fibers are present above the drain. Free water is present below the drain, and remaining water is saturated in the interstitial spaces of the fibrous material. In MSW systems, little, if any, free water is present above the fibrous material. Above the fibrous material, the free space contains high-pressure steam.

In the present invention, when a screened drain is opened at or near the bottom of the vessel, the region around the drain flashes into steam. The steam, as it is trapped by the overhead confining fibrous material mat, explosively escapes toward the drain, thereby entraining and driving additional interstitial water toward the drain.

At the same time, the high-pressure gradient on top of the fibrous material and the drain acts effectively as a pressure filter, forcing interstitial water toward the drain.

This process of pressure-entrainment-extraction of water, combined with evaporation, continues until the filter cake clogs and becomes essentially non-porous. At that time, a simple rotation of the vessel may be carried out to break up the filter cake (and/or, the vessel is tilted and a second valve is opened), and the process is repeated until the vessel and its residual contents have cooled (from the conversion of sensible heat to latent heat) to below the ambient pressure boiling point of water.

Accordingly, another aspect of the present invention is the provision of a high vessel pressure (typically above about 5 atmospheres) to assist in the dewatering and drying of the vessel contents. Experimentation has shown that a residual water concentration below about 20% is achievable. The present invention thus allows for the vessel to be re-pressurized with air or steam to assist in the pressure-forced removal of water.

The present invention also includes a method of dewatering a processed or processing waste stream mass on the type to which the invention relates, such as processed or processing waste stream mass comprising a substantial amount of cellulosic materials or other materials that entrain water, such as interstitial water.

The method of the present invention thus includes a method of processing solid waste products in a vessel, comprising loading the vessel with a charge of solid waste products along the bottom of the vessel; sealing the vessel; introducing steam into the vessel so as to pressurize the vessel; rotating the vessel so as to cause the charge of solid waste products to be moved from the bottom of the vessel to toward the top of the vessel; periodically removing aliquots of liquid water from the vessel; and thereafter depressurizing the vessel and unloading the processed solid waste therefrom. It is preferred that the vessel remains pressurized during the removal of aliquots of water, and that the water is removed from a point below the mass such that aliquots of liquid water or steam are forced from the mass vessel remains pressurized during the removal of aliquots of water.

It is also preferred that the water is bound in the charge of solid waste products, and the pressure with the vessel is cycled between a lower pressure by the exhaustion of steam to cause the evaporation of the bound water, and a higher pressure by the introduction of steam. Typically, the lower pressure is in a range of from about 5 psia to about 15 psia.

Preferably, the vessel comprises a valve disposed on one side of the center axis thereof and one end of the vessel is positioned lower than the opposite end prior to the removal of an aliquot of liquid water from the vessel.

The present method also includes dewatering processed or processing solid waste products in a vessel, by loading the vessel with a charge of solid waste products along the bottom of the vessel; sealing the vessel; introducing steam into the vessel so as to pressurize the vessel; processing the charge of solid waste products so as to form a mass having water therein and an upper boundary, and having a pressurized space thereabove within the vessel; periodically opening the vessel from a point below the mass such that aliquots of liquid water or steam are forced from the mass while the vessel remains pressurized; and thereafter depressurizing the vessel and unloading the processed solid waste therefrom.

Apparatus with Water Exhaustion Valves

The invention also includes an apparatus for processing solid waste products, the apparatus comprising a rotatably mounted cylindrical vessel adapted to contain a waste product mass having an upper boundary, and having a first end, a second end and an interior surface, at least one end terminating in a hatch that may be opened to allow access to the interior of the vessel and sealably closed to allow pressurization of the vessel; a steam inlet for injecting steam into at least one of the ends; and at least one valve disposed at a position so as be adapted to exhaust water or steam from a point below the upper boundary. It may be desirable to provide the vessel with a plurality of valves disposed about its outer cylindrical circumference. Optionally, the valve(s) may be connected to a pump or similar equipment adapted to draw fluid from the vessel.

DETAILED DESCRIPTION OF THE PREFERRED EMBODIMENT

In accordance with the foregoing summary, the following provides a detailed description of the preferred embodiment, which is presently considered to be the best mode thereof.

The invention relates to a process for recycling waste. This process is sterilizing high density materials such as glass, plastics, metals and recovering others from municipal solid waste (MSW) and converting paper, cardboard, food waste, etc. to a usable fiber and separating it from other recyclable materials.

Figure 1:
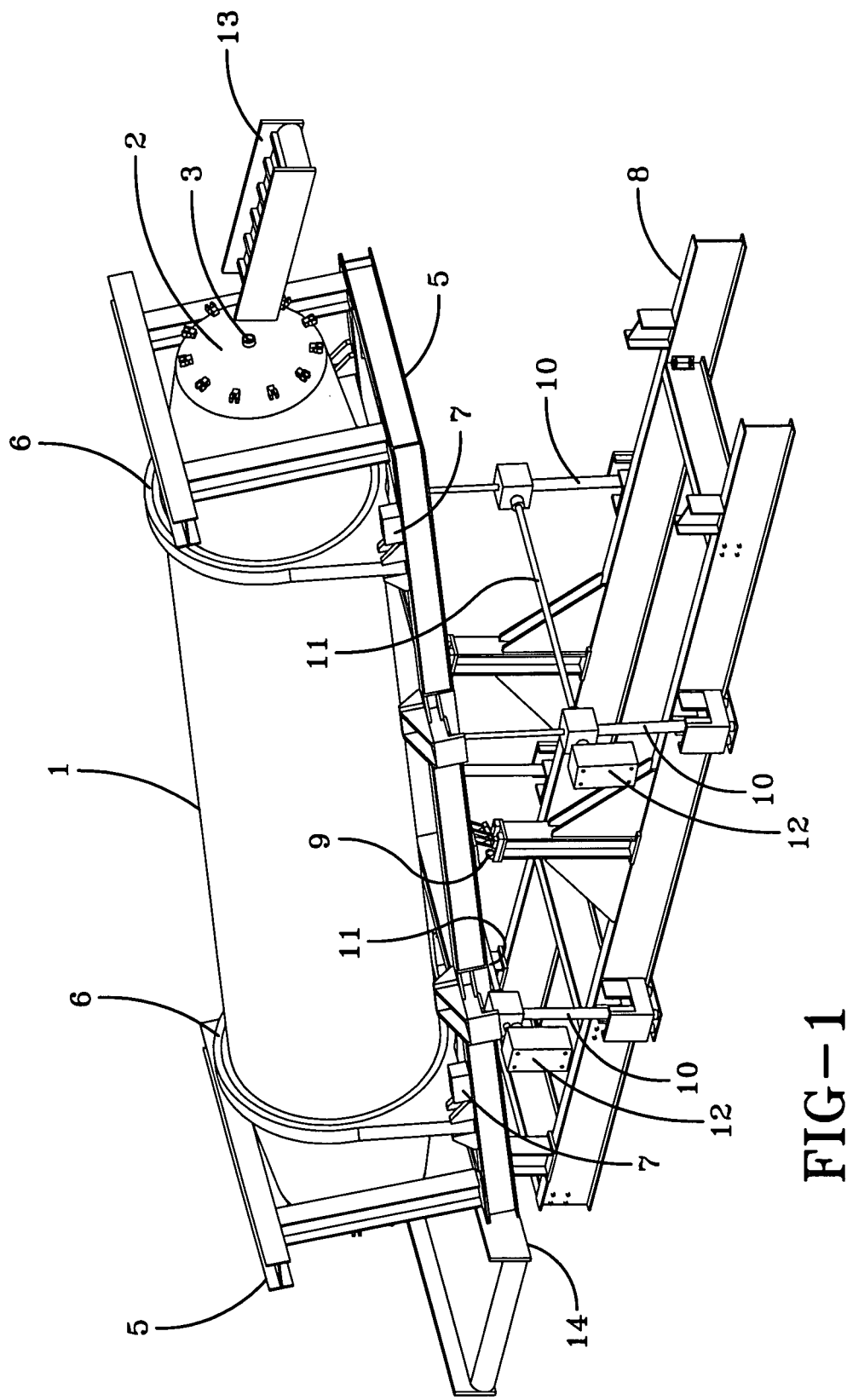
FIG. 1 is a perspective view of an apparatus for processing solid waste products in accordance with one embodiment of the present invention.

FIG. 1 shows an example of an apparatus for processing solid waste products in accordance with one embodiment of the present invention.

FIG. 1 shows a rotatably mounted cylindrical vessel 1 having a first end, a second end and an interior surface, at least one end terminating in a hatch 2 that may be opened to allow access to the interior of the vessel and sealed closed to allow pressurization of the vessel. It is preferred that the vessel have a hatch on either end such that the vessel may be opened to allow access to the interior of the vessel and sealed closed to allow pressurization of the vessel the charge of waste products, and so that it may be loaded one end and removed at the other end. This may be done, for example, by using a ram that may push the treated charge from the vessel by extending through the vessel.

Also shown in FIG. 1 is a steam inlet 3 for injecting stem disposed at least one of the ends, and preferably at both ends. Steam inlet 3 may be connected to steam conduits (not shown) so as to introduce and maintain steam pressure into the vessel.

The vessel may be rotated with respect to upper frame portion 5, such as by virtue of mechanical sleeve drives 6. The apparatus also includes at least one motor or other means for rotating the vessel.

The motor(s) 7 may otherwise be connected to the vessel through appropriate drive/transmission means, such as to sprocket by a chain or belt.

Typically, the motor and drive means will be mounted in such an arrangement so as to move along with the movement of the vessel itself, such as by being mounted on a moveable frame 5 supporting the vessel.

Upper frame portion 5 in turn is supported by lower frame portion 8 that includes fulcrum pivot portion 9. Also shown in FIG. 1 are the mechanical screw actuators 10 on either side of fulcrum pivot portion 9 that move the vessel 1 between a position wherein the first end is higher than the second end and a position wherein the second end is higher than the first end. This movement allows the operator to balance the load of the charge of waste products both before and during the steam treatment and to agitate the charge longitudinally. Longitudinal agitation provides the ability to distribute cold spots that may develop in the waste charge mass, thus providing a more uniform heating of the charge. The actuators 10 may be linked in tandem across frame 8 by drive rods 11 that are driven be respective electric motors 12.

The actuators 10 may include load sensors to determine the state of balance of the charge of waste products as originally loaded. Should the charge of waste products be determined to be out of balance upon initial loading, the actuators 10 may be used to redistribute the load to even its balance, either through back-and-forth oscillation or through rapid agitation, to cause the charge of waste products to shift in position within the vessel. The load sensors may provide signals or information to a microprocessor or PLC controller that is provided with programming instructions to access the load at each sensor, and to provide feedback instructions to the actuators.

FIG. 1 also shows rotatably mounted cylindrical vessel 1 with the first end raised with respect to the second end, such as would be the position for loading the vessel with the aid of input conveyor 13. This position may also be used to discharge the waste products after treatment onto discharge conveyor 14, or to urge the charge of waste products toward the second end in order to level the load of waste products during processing. The position of vessel 1 may of course be varied along the range of positions from horizontal to any angle between the maximum tilt angle shown in FIG. 1, and its corresponding opposite.

Figure 1A:
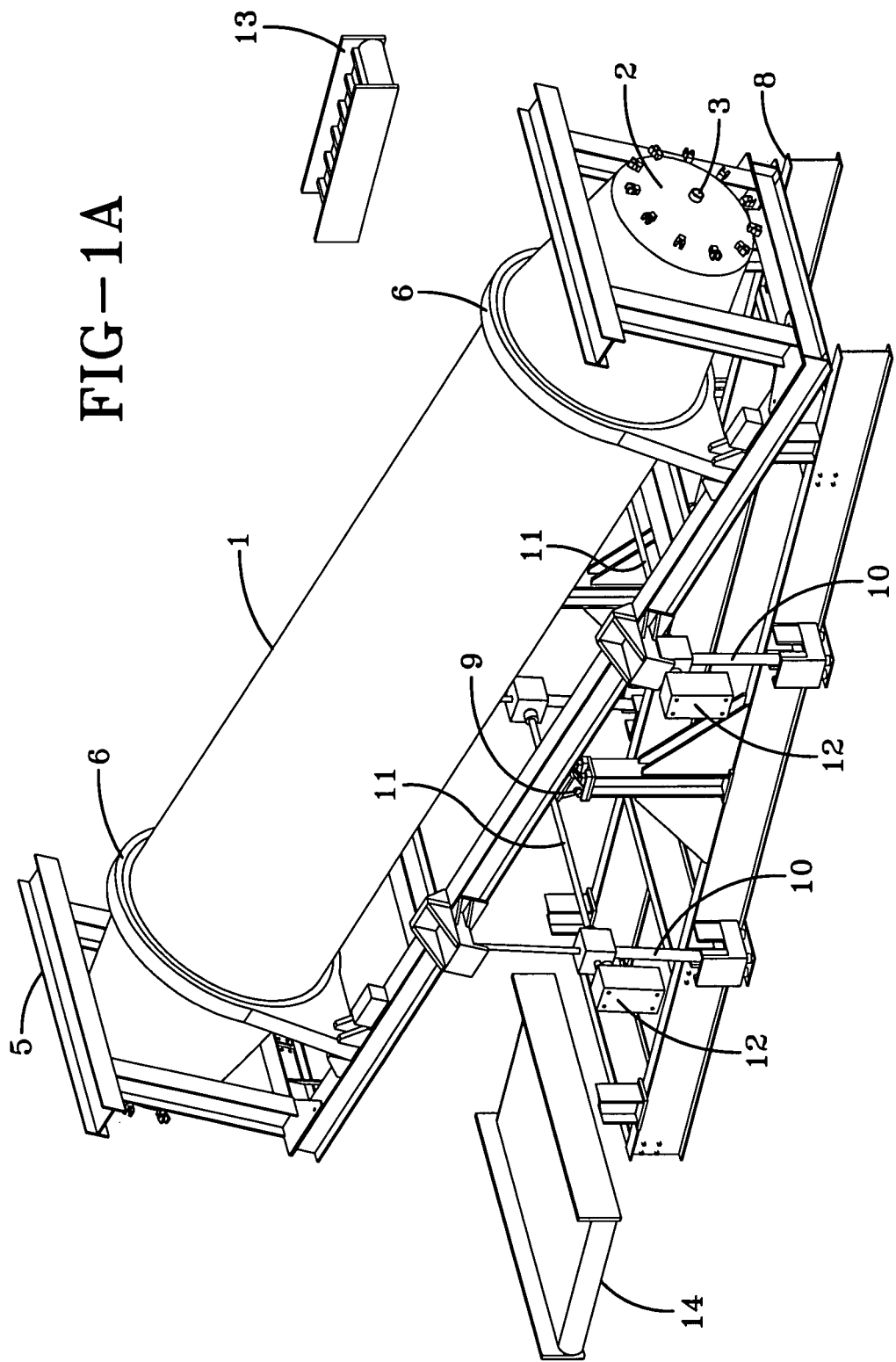
FIG. 1a is another perspective view of an apparatus shown in FIG. 1.

FIG. 1*a* is another perspective view of an apparatus shown in FIG. 1, showing the discharge or second end lower than the input or first end.

Figure 3:
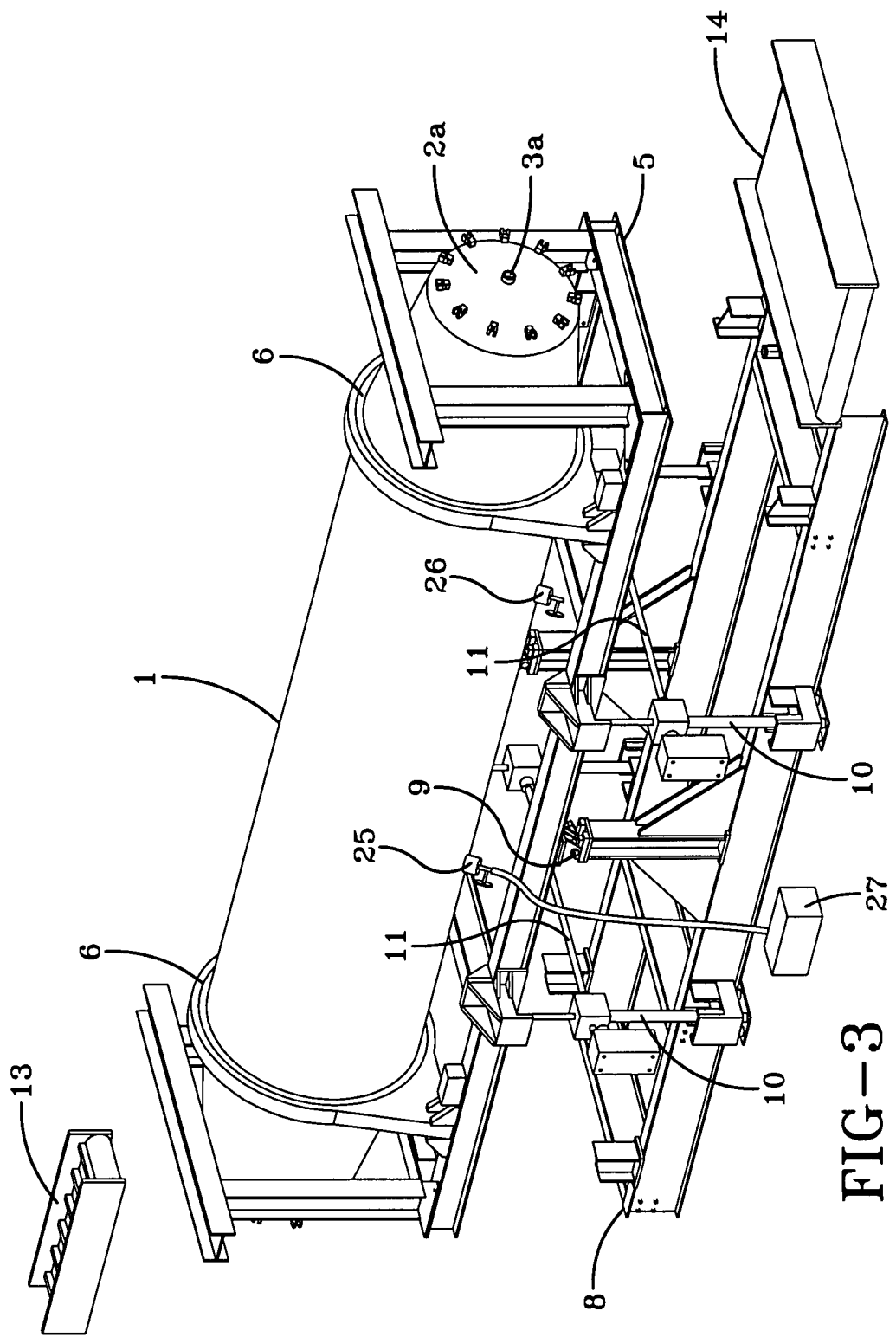
FIG. 3 is another perspective view of an apparatus for processing solid waste products in accordance with one embodiment of the present invention.

FIG. 3 shows, using the same reference numbers shown in FIG. 1, a rotatably mounted cylindrical vessel 1 as depicted in FIG. 1 with the first end and the second end at about the same height such that the vessel is horizontal. This position is typical of those at which the vessel would be maintained during operation, with relatively small adjustments being made to urge the charge of waste products toward either end in order to level the load of waste products. This view also shows the second hatch 2*a* (having steam inlet 3*a*) which is used as an exit hatch for the treated waste product charge.

Figure 4:
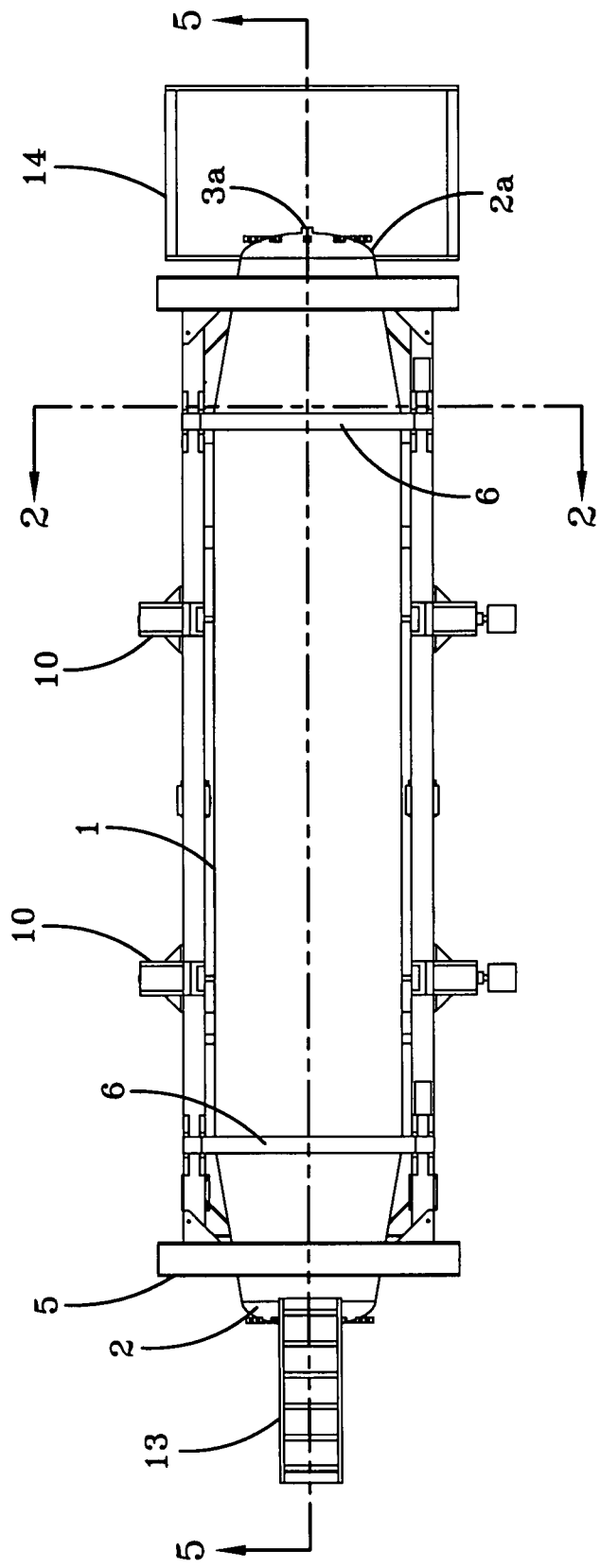
FIG. 4 is a plan view of an apparatus for processing solid waste products in accordance with one embodiment of the present invention.

Conversely, FIG. 4 shows a top plan view of the rotatably mounted cylindrical vessel 1 as depicted in FIG. 1 with the second end raised with respect to the first end, such as may be necessary to move the charge of waste products toward the first end in order to level the load of waste products.

Figure 2:
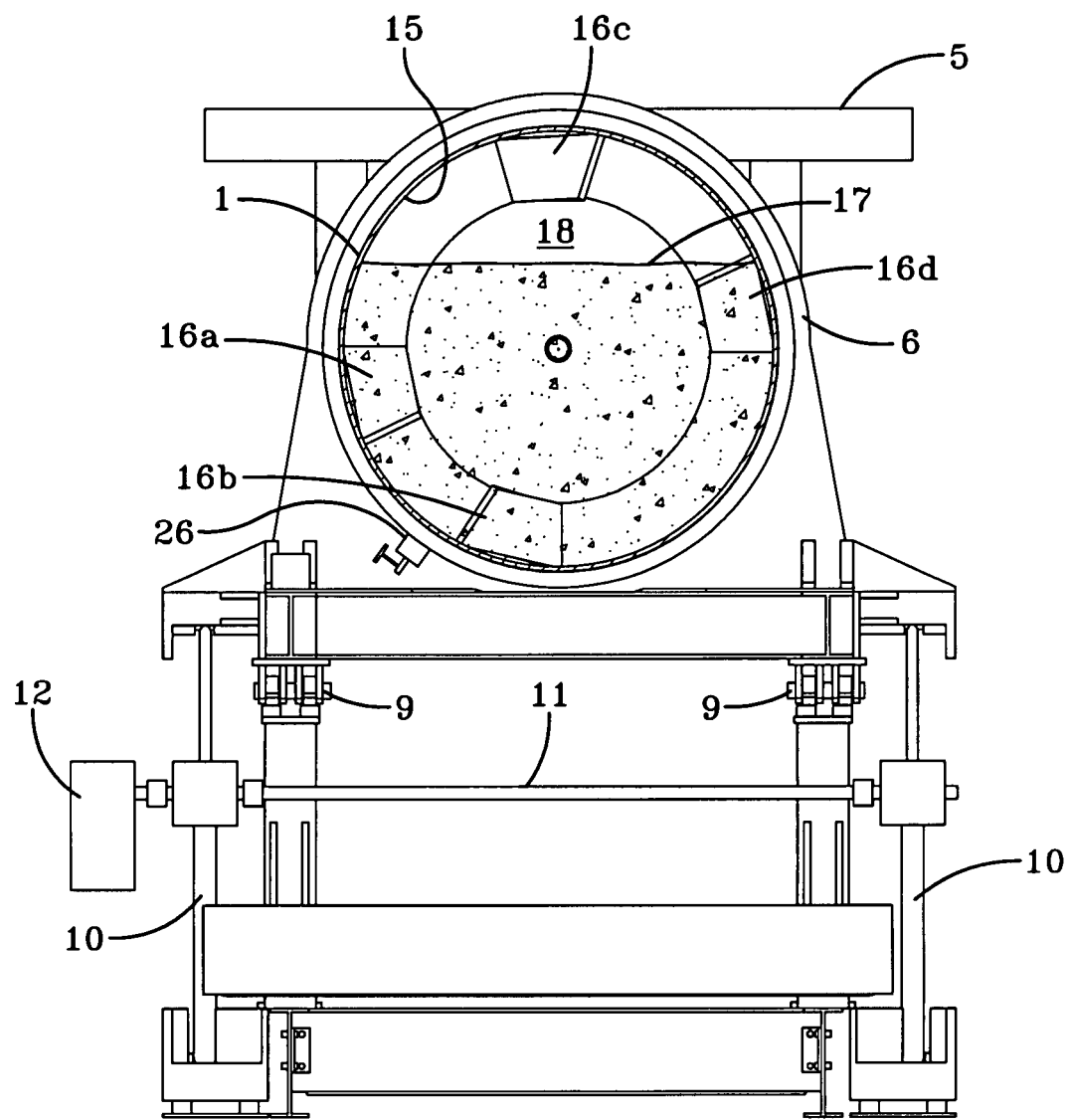
FIG. 2 is a cross section view of the vessel for processing solid waste products in accordance with one embodiment of the present invention.
Figure 5:
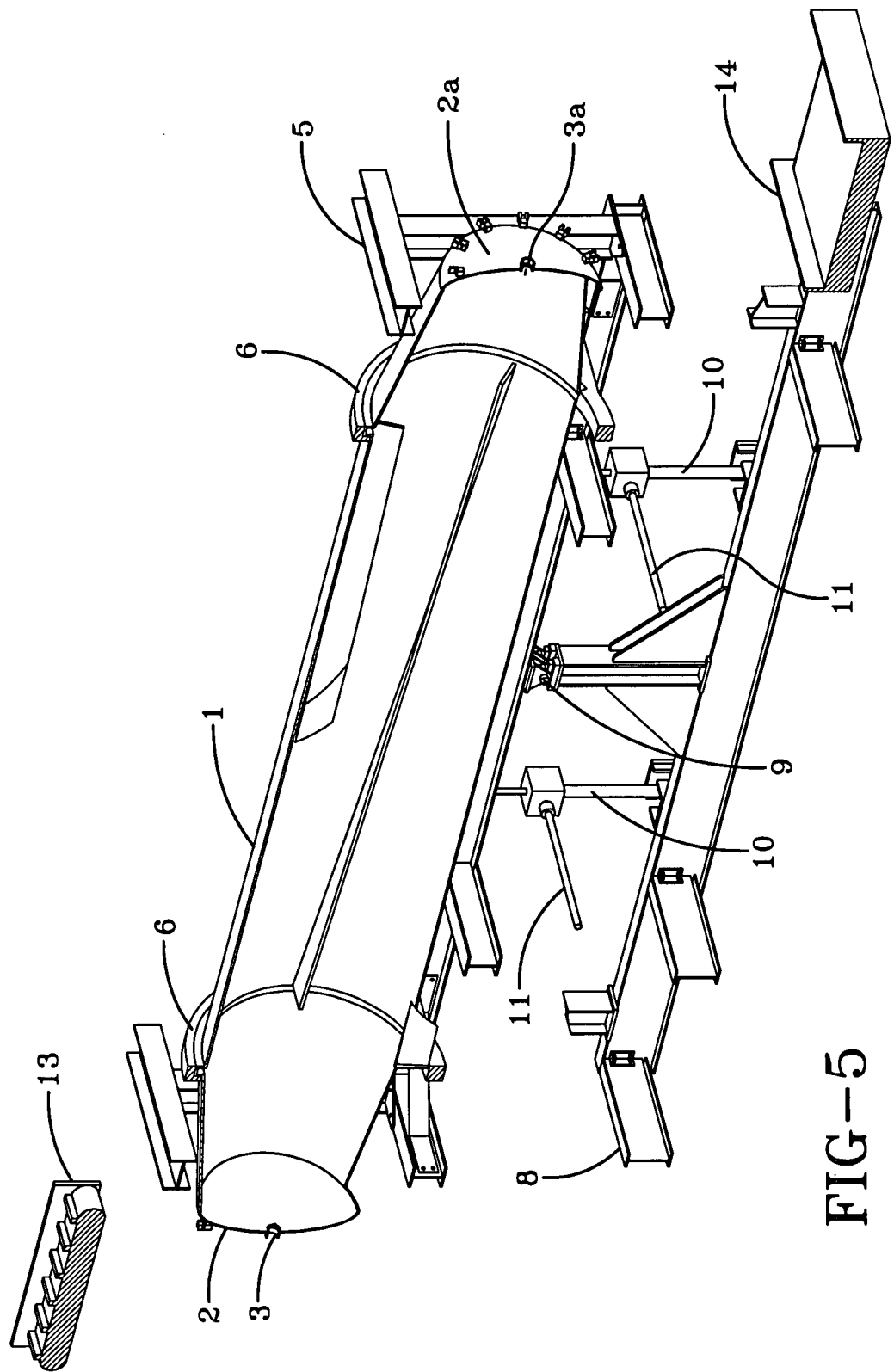
FIG. 5 is a cross section view of the vessel for processing solid waste products in accordance with one embodiment of the present invention.

FIG. 5 is a longitudinal cross section view of the vessel system for processing solid waste products in accordance with one embodiment of the present invention, using the same lead lines from the FIGS. 1 and 2 and taken along line 5-5 of FIG. 4. FIG. 5 shows the angling of one of the blades such as 16*a*-16*d*) shown in FIG. 2 (a cross-section along line 2-2 of FIG. 4), and also shows that neighboring pairs of blades converge alternately toward opposite ends of the vessel. This view also shows that the vessel may additionally comprise frusto-conical sections at either end to assist in loading and unloading the vessel, and to help maintain portions of the charge of waste products oriented in the portion of the vessel provided with the blades for agitation. FIGS. 2 and 5 also show that the blades are preferably slightly twisted such that ends of adjacent blades that converge are twisted away from one another while ends of adjacent blades that diverge are twisted toward from one another.

Figure 8:
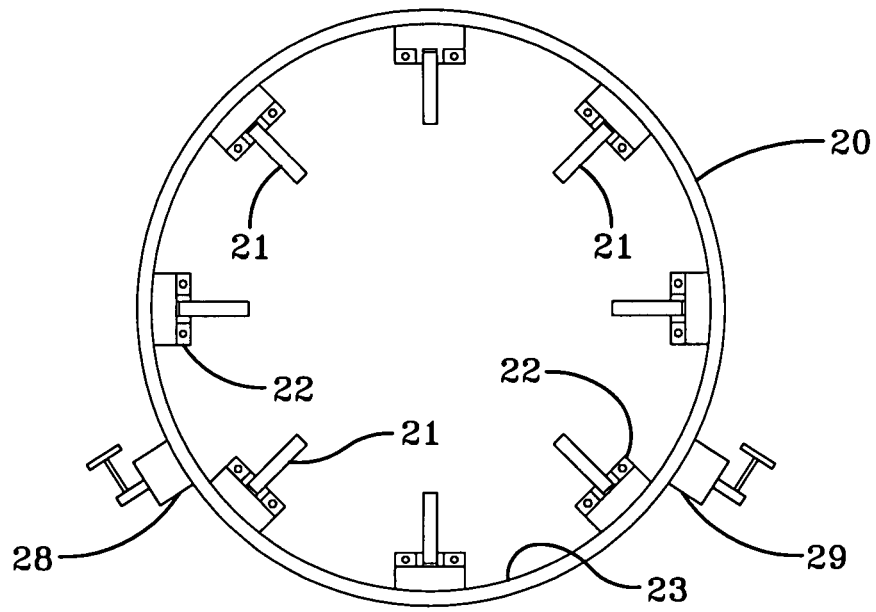
FIG. 8 is a longitudinal view of the cylindrical portion of a treatment vessel, and shows an alternative embodiment of the present invention wherein a plurality of straight blades are used in the vessel.
Figure 9:
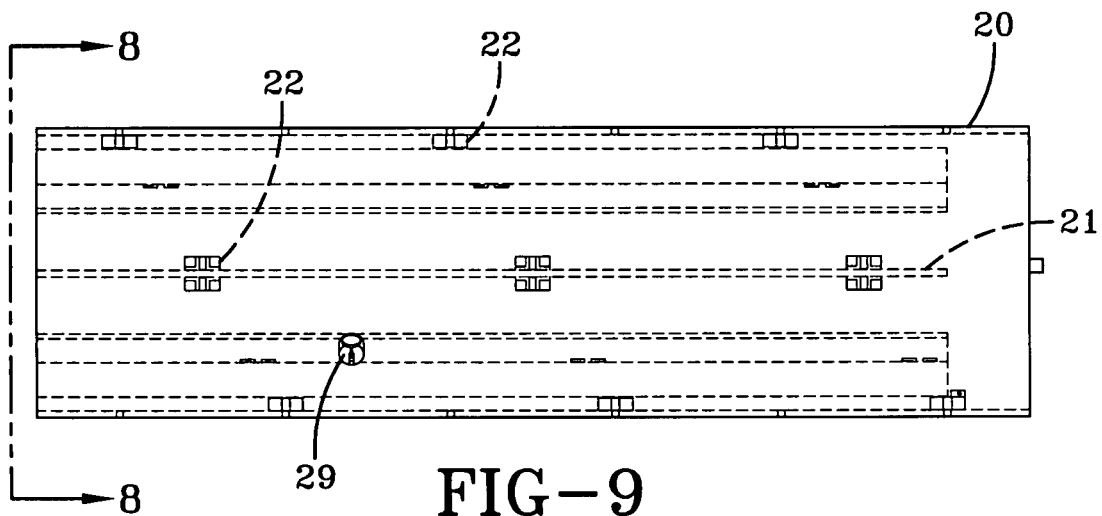
FIG. 9 is an elevation view of the cylindrical portion of a treatment vessel, and shows an alternative embodiment of the present invention wherein a plurality of straight blades are used in the vessel.
Figure 10:
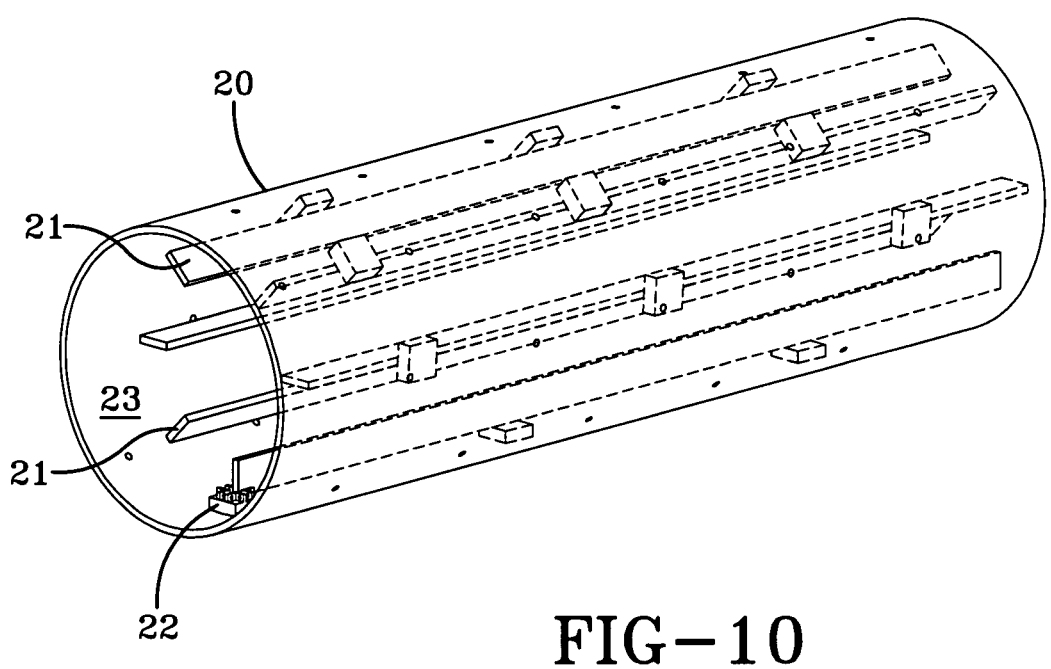
FIG. 10 is a perspective view of the cylindrical portion of a treatment vessel, and shows an alternative embodiment of the present invention wherein a plurality of straight blades are used in the vessel.

FIGS. 8, 9 and 10 show views of the cylindrical portion of a treatment vessel as described herein, and shows an alternative embodiment of the present invention wherein a plurality of straight blades are used in the vessel.

FIG. 8 shows a longitudinal view of the cylindrical portion of a treatment vessel 20 in place of vessel 1 as described herein, wherein a plurality of straight blades 21 is used in the vessel. The blades 21 are mounted on individual mounting brackets 22 that serve to hold the blades 21 away from interior surface 23. FIG. 8 is a view taken from line 8-8 of FIG. 9. The mounting brackets 22 may also be used to mount the twisted blades as described herein.

FIG. 9 is an elevation view of the cylindrical portion of a treatment vessel 20, and shows in phantom a plurality of straight blades 21 and mounting brackets 22 holding the blades 21 away from interior surface 23. FIG. 9 also shows a plurality of substantially straight blades 21 protruding from the interior surface of the vessel, and each blade extending substantially the entire length of the vessel, so as to be capable of transporting waste material from the bottom of the vessel toward the top of the vessel, and releasing the waste material to fall to the bottom of the vessel.

FIG. 10 is a perspective view of the cylindrical portion of a treatment vessel 20, and shows in phantom a plurality of straight blades 21 and mounting brackets 22 holding the blades 21 away from interior surface 23.

Figure 6:
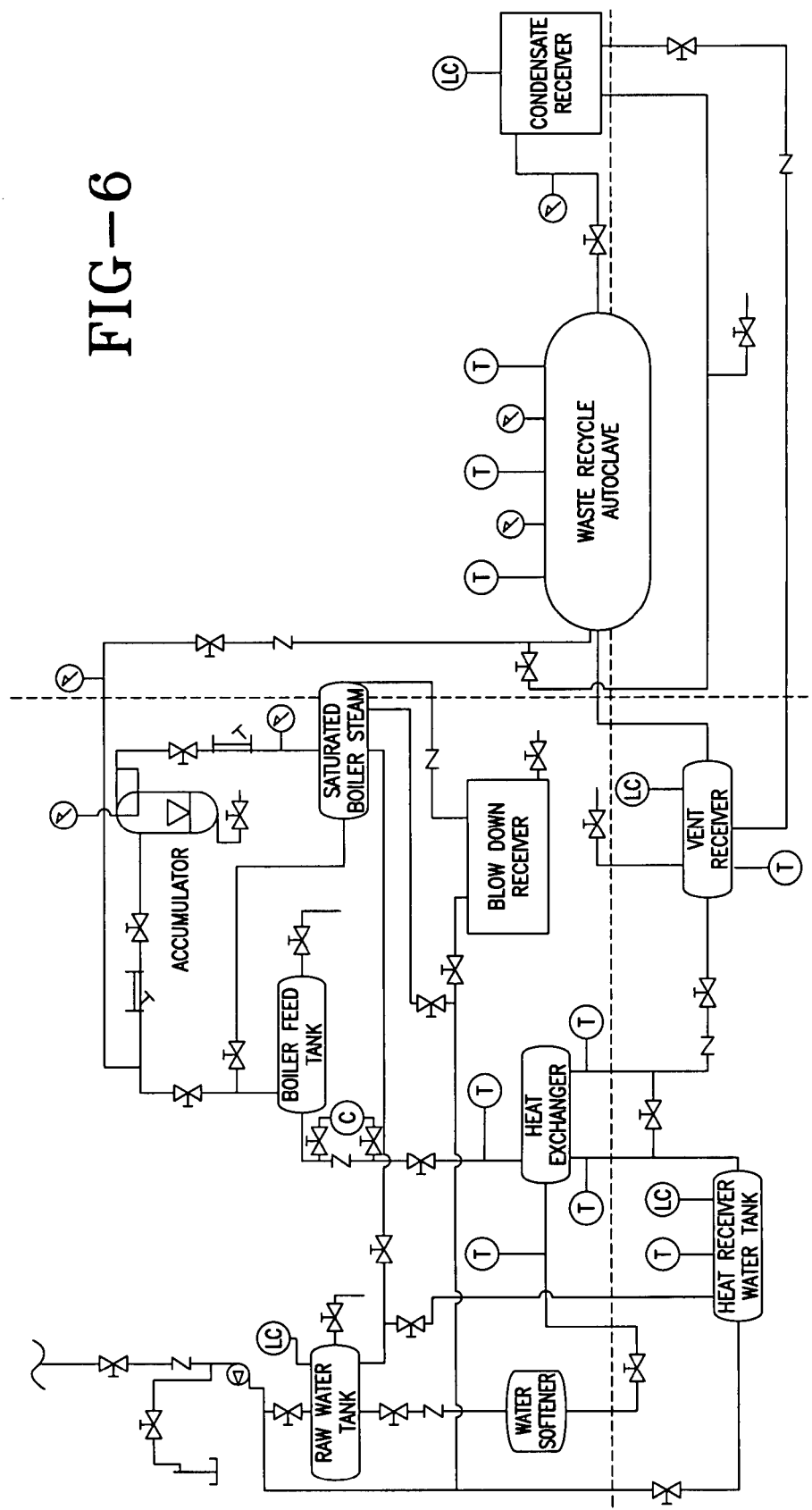
FIG. 6 is a schematic of a waste processing system with which the present invention may be used, for processing solid waste products in accordance with one embodiment of the present invention.

FIG. 6 is a schematic of a waste processing system with which the present invention may be used, for processing solid waste products in accordance with one embodiment of the present invention that permits one-way steam flow through the vessel. This figure shows the various components of a system designed to provide the vessel with steam, and the ancillary components of the preferred embodiment. This figure also shows the positions of valves and gauges using standard indicia, such as control valves, check valves, thermocouples, strainers, pressure gauges, motors and pumps.

Figure 7:
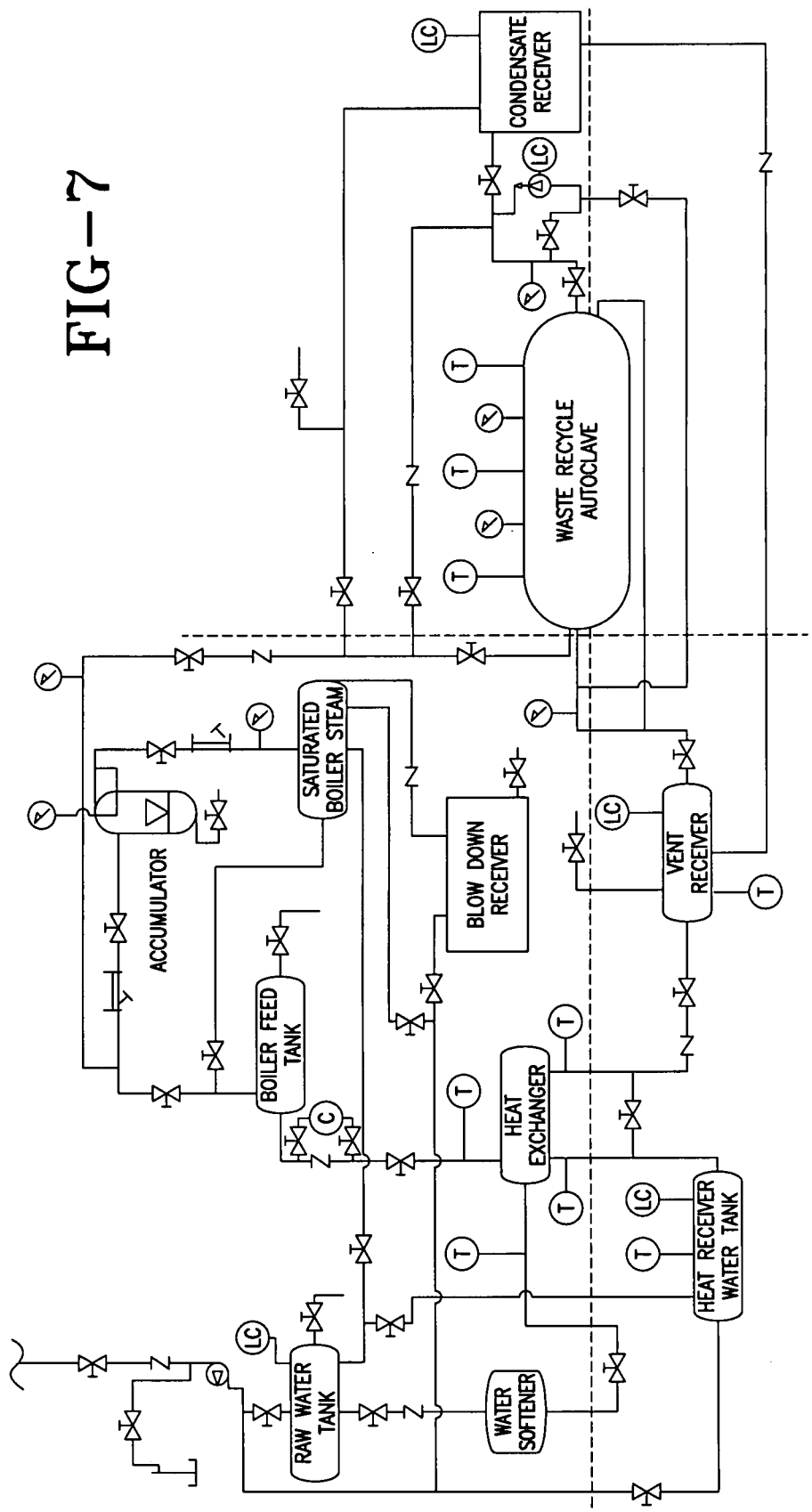
FIG. 7 is a schematic of a waste processing system with which the present invention may be used, for processing solid waste products in accordance with another embodiment of the present invention.

FIG. 7 is a schematic of a waste processing system with which the present invention may be used, for processing solid waste products in accordance with another embodiment of the present invention that permits two-way steam flow through the vessel that may be provided in pulses. This figure also shows the positions of valves and gauges using standard indicia, such as control valves, check valves, thermocouples, strainers, pressure gauges, motors and pumps. This schematic provides an example of a system that permits steam, particularly superheated steam, to be provided in pulses to the vessel of the present invention.

The views of FIGS. 3 and 4 are used for illustrative purposes only, and it will be understood that the vessel may be titled to lesser degrees during processing in order to make lesser adjustments in the load distribution through leveling, and that such movement may be relatively rapid or slower and/or repetitive, depending upon the load situation presented.

FIG. 2 also shows an example of a line 17 representing the top of a waste product charge as it would appear once leveled within the vessel 1. The waste product charge leaves a zone of space 18 above it such that a steam region extends the length of the vessel through which successive portions of the waste products will pass as the vessel rotates. It is preferred that the interior of the vessel be substantially free of structure presenting surfaces that are not substantially parallel to the central longitudinal axis of the vessel.

The operation of the vessel can be appreciated from the cross-section of the apparatus shown in FIG. 2 showing vessel 1, interior surface 15 and blades 16a-16d.

The blades may be straight and substantially parallel to the longitudinal axis of the vessel, or, as shown in FIG. 2, preferably may be angled such that neighboring blade pairs (e.g., 16a and 16b) converge toward one end of the vessel, while successive blade pairs (e.g., 16b and 16c) converge toward the opposite end of the vessel, as seen in FIG. 2. The straight blades permit portions of the waste charge to be raised vertically and dropped vertically as the vessel rotates. The angled blades as described above further cause an alternating side-to-side movement of successive portions of the waste charge, as the vessel rotates, by allowing successive portions of the waste charge to fall at an angle to the vertical such that the successive portions are moved gently from side to side without compaction.

After the vessel is loaded with the charge of waste products, the door through which the charge was loaded is shut, steam is introduced continually into the vessel, and the vessel becomes pressurized. Fresh steam may be continuously fed into the vessel from the loading end, and after a predetermined processing pressure is reached, steam may be allowed to escape the vessel into the discharge steam line.

The temperature and pressure of the vessel are monitored, and the flow of steam is regulated to keep the process within predetermined processing ranges (typically around 70-100 psi, at 300-335° F.). The vessel is rotated at a predetermined speed (depending on the size of the vessel), and after a requisite time and temperature profile is achieved amount of time (typically 20 to 45 minutes), the pressure is released and the processed waste is removed.

The temperature of the charge of waste products may be monitored by thermometers or thermocouples disposed along the length of the vessel. The temperature readings are taken and applied to determine the temperature of portions of the charge of waste products. The thermometers or thermocouples may provide signals or information to a microprocessor or PLC controller that is provided with programming instructions to access the temperature at each thermometers or thermocouples, and to provide feedback instructions to the actuators. This information may be used as feedback control to the actuators 9 in order to adjust the charge of waste products within the vessel so as to increase heat transfer to portions of the charge not receiving effective heat treatment, in order to maintain overall efficient heat transfer to the charge of waste products overall.

A given charge of waste products may contain a wide variety of constituents, such as wood, paper, organic matter, water, etc. Each charge of waste products presents its own heat capacity and transfer profile, while there is required an overall heat absorption of the mass in order to provide an effective treatment of the waste products charge.

The information from the thermometers or thermocouples may also be used to determine the heat absorption over time as the charge of waste products heats up initially. This allows the operator (or a microprocessor or PLC controller) to extrapolate the energy needs for that charge of waste products and, based upon a comparison of the heat transfer profile, to also determine the approximate qualitative constituent make-up of the charge of waste products, and thus allow the determination of the treatment time necessary to treat that particular charge.

In operating the vessel of the present invention, the vessel may be tilted so as to present the input hatch 2 upward with respect to the horizontal, and to allow a charge of waste products to be placed into the vessel with the aid of conveyor 13. The hatch 2 is then closed and the waste products 17 charge (see FIG. 2) may optionally be leveled by a reciprocating action of the actuators 10 prior to introduction of steam, or upon initial introduction of steam.

Once the hatch 2 is sealed, steam is placed into the vessel through inlets 3 and/or 3a to provide a pressurized steam environment in the vessel 1. Examples of systems used to produce and inject the steam are shown in FIGS. 6 and 7.

The vessel 1 is then rotated and the blades 16a-16d (or blades 21 in FIGS. 8-10) act to raise portions of the waste products charge 17 from the bottom to the top of the vessel, and then release them to fall through the a zone of the steam environment 18 of relatively low density (i.e., that space not occupied by the waste products 17 as seen in FIG. 2. This zone increases in volume as the waste products 17 shrinks during the processing.

The cylindrically shaped vessel 1 has a number of blades to function as a stirring apparatus to homogenize heat and circulate the waste vertically and/or horizontally, and at least one opening to load and discharge waste (i.e., hatches 2 and 2a, respectively). The conical structures at the openings enhance the input of the waste products charge and the discharge of the treated waste. These structures also serve to maintain the waste in the central horizontal region of the vessel. The vessel may be titled by its longitudinal axis with respect to the horizontal position for effective waste loading into the vessel by the gravity force. This tilting may also be used during the processing to level the waste products charge.

According to the invention, steam inlets are connected to one or more saturated or superheated steam supply and to a steam receiver. In this way, the vessel is pressurized and depressurized from one or more openings. Each opening may be provided with a pressure lock and bidirectional steam flow conduits and valves. The apparatus may also include an optional steam vacuum pump at each opening for rapid depressurizing of the vessel. Rotating union valves may also be included to enable steam flow in-out of the vessel as the vessel is rotating or tilting. These features are shown schematically in FIGS. 6 and 7.

Load cells that are attached to or independent of the actuator(s) and connected to the frame structure detect when the process material within the vessel is non-uniformly distributed along the vessel's horizontal axis. Uniform distribution of waste in the vessel is attained by rotating the vessel on its latitude axis in accordance with and by the reference to load cell signals.

As the vessel rotates, the temperature is monitored to determine the change in temperature of the waste products charge over time. A plurality of temperature sensors may be used to send feedback to the control to achieve homogenous temperature in the vessel. The feedback control system and controller may include PLC or microprocessors that accept data from the temperature and load sensors and provide feedback control to the vessel rotation and the actuators to reposition and redistribute the waste charge load as required for efficient processing.

It is preferred that the heated and pressurized vessel is rotated bidirectionally, and at a constant or variable speed depending on the waste type, to attain homogenous heat transfer during the treatment cycle. As the waste shrinks due to the pressure and temperature, the volume of the waste charge decreases. The open space, such as the volume of space 18, increases by shrinkage in the vessel and serves as a hot region to provide heat treatment to portions of the waste charge that are raised and allowed to fall through this relatively low density region. This provides most complete and efficient exposure of the waste to the steam environment.

This temperature data may also be used to determine the overall absorption of energy over time which in turn allows the operator to characterize the waste products qualitatively (e.g., in terms of overall makeup of organic matter, paper, etc.) through pre-determined data on waste product constituents, and thereby to extrapolate the amount of time a given charge of waste products will require to complete processing. This information may be stored and fed back into the control system to determine a time when the processing may be stopped automatically or through a signal to the operator.

As a result of steam condensation during this process, sludge may develop, and to avoid mixing the recycled waste with the sludge, one or more gaps or perforations may be provided in the blades (preferably near the interface between the blades 16a-16d and the interior surface 15; see e.g. blades 16b and 16d having perforations and gaps, respectively) to allow the sludge to remain at the bottom of the vessel and the stirring mechanism and the chamber keeps the sludge at the bottom of the vessel. This may also be done by using the mounting arrangement shown in FIGS. 8-10. The perforations shown in FIG. 2 may also be used in the straight blades shown in FIGS. 8-10, and the mounting arrangement shown in FIGS. 8-10 may also be used with the blade type and arrangement shown in FIG. 2.

Due to the fact that the amount of sludge would vary depending on the steam type and quality, superheated, dry steam, may be used in place of conventional saturated steam to reduce the amount of sludge.

Also, during rotation of the vessel, the thermocouples determine whether the waste products charge has developed relatively cold regions, such as through the make up of the charge itself, or through compaction, that is retarding the rate of heat transfer to that region. If a relatively cold region is detected, the vessel may be tilted and/or oscillated by the actuators to redistribute the mass along the length of the vessel. Also, in the event the waste products charge otherwise becomes unbalanced, the actuators may tilt and/or oscillate the vessel to redistribute the mass along the length of the vessel. This may be done through PLC controllers or microprocessors operating in conjunction with the thermocouples and actuators.

Through the action of the actuators, the waste charge can be maintained relatively evenly distributed along the length of the vessel during processing, so that the blades are able to raise portions of the waste products charge that are substantially uniformly distributed along the length of the vessel, and to allow those portions to descend through a relatively low density zone created and maintained along the length of the treatment volume of the vessel.

The tilting pivot point is preferably located at the center of gravity to balance the weight at horizontal position and to incline the vessel at an adjustable bidirectional angle relative to its horizontal position. Mechanical linear actuators, chain systems, hydraulic actuators, pinion rack systems, and scissors systems, etc. are types of mechanisms that may be used in providing the tilting movement.

This system therefore prevents and dynamically rectifies unbalanced loads and any other sources of localized compaction of the waste products charge, and allows efficient treatment of the waste products charge by creating and maintaining a low density zone through which individual portions of the waste products charge are passed with increased efficiency and without compaction of portions of the waste products charge as occurs in other treatment vessel systems with active transport systems or vessels that permit portions of the waste products charge to remain compressed or in a state of non-uniform distribution.

Another aspect of the present invention relates to water exhaustion during processing. An example of the method and apparatus of this aspect of the present invention may be appreciated by reference to FIGS. 2 and 3. These Figures show one or more optional valves placed so that they may be opened to exhaust water, typically in the form of a mixture of water and steam, to be exhausted from below the waste mass being processed. As may be appreciated from FIG. 2, when the valve 26 is opened while the vessel is pressurized, the pressure of the steam in region 18 causes any water collected at the bottom of the vessel 1 (and progressively any interstitial water in the mass 17), to be exhausted (at these operating pressures in the form of steam). This exhaustion is then preferably followed by repeated cycles for pressurizing the vessel and further processing the waste mass, followed by further water exhaustion cycles. This process leads to a dryer processed mass upon completion of the time/temperature process cycle that is necessary to effectively render the waste mass to the physical and chemical characteristics desired.

FIG. 3 shows valves 25 and 26. These valves may be of any type appropriate for the function. Preferably, they may be fitted with means, such as screens that allow water and steam to be exhausted as described herein while preventing fouling of the valve opening. The water may be evacuated to atmospheric pressure, or may even be evacuated under the influence of vacuum such as through the use of vacuum pump 27 attached to valve 25 as shown in FIG. 3.

The valves may also be placed in a series around the vessel such that the vessel may be halted at any point such that a valve is positioned at or near the bottom of the vessel, or otherwise at a point below the upper boundary of the waste mass within the vessel. An example of such as arrangement is shown in the position of the valves 28 and 29 in FIG. 8, although more valves may be added to form a series about the circumference of the vessel.

It is apparent that while specific embodiments of the invention are disclosed, various modifications of the apparatus or parameters of the process may be made which will be within the spirit and scope of the invention. Therefore the spirit and scope of the present invention should be determined by reference to the claims below.

What is claimed is:

1. A method of processing solid waste products in a vessel, said vessel including a valve, said method comprising:
   loading the vessel with a charge of solid waste products along the bottom of said vessel;
   sealing the vessel;
   introducing steam into said vessel so as to pressurize said vessel;
   rotating said vessel so as to cause said charge of solid waste products to be moved from the bottom of said vessel to toward the top of said vessel, whereby some of said steam contacts said solid waste products and condenses as liquid water within said vessel;
   periodically halting the rotation of said vessel such that said solid waste products settle to the bottom of said vessel and said liquid water forms a water line within said vessel and such that said valve is disposed below said water line, and opening said valve from the outside of said vessel and removing aliquots of said liquid water from said vessel while said vessel is pressurized; and
   thereafter depressurizing the vessel and unloading the processed solid waste therefrom.

2. A method according to claim 1 wherein said liquid water is drawn from said vessel by a pump adapted to draw said liquid water from said vessel.

3. A method according to claim 1 wherein said water is removed from a point below said charge of solid waste products such that aliquots of liquid water are forced from said charge of solid waste products while said vessel remains pressurized during said removal of said aliquots of water.

4. A method according to claim 1 wherein said vessel is maintained at a temperature of from about 300 degrees to about 335 degrees Fahrenheit.

5. A method according to claim 1 wherein the pressure with said vessel is maintained in the range for from about 70 to about 110 psia.

6. A method according to claim 1 wherein water is bound in said charge of solid waste products, and wherein the pressure with said vessel is cycled between a lower pressure by the exhaustion of steam to cause the evaporation of said bound water, and a higher pressure by the introduction of steam.

7. A method according to claim 6 wherein said lower pressure is in a range of from about 5 psia to about 15 psia.

8. A method according to claim 1 wherein water is bound in said charge of solid waste products, and wherein, after removal of an aliquot of liquid water, the pressure with said vessel is cycled between a lower pressure by the exhaustion of steam to cause the evaporation and expansion of said bound water, and a higher pressure by the introduction of steam.

9. A method according to claim 8 wherein said lower pressure is in a range of from about 5 psia to about 15 psia.

10. A method according to claim 1 wherein said aliquots of liquid water are recycled to create steam which is reintroduced into said vessel.

11. A method according to claim 1 wherein said steam is superheated steam introduced in pulses into said vessel.

12. A method according to claim 1 wherein said vessel comprises a valve disposed on one side of the center axis thereof and wherein said one side of said vessel is positioned lower than the opposite side prior to the removal of an aliquot of liquid water from said vessel.

\* \* \* \* \*